United States Patent
Bieler et al.

(10) Patent No.: US 9,692,324 B2
(45) Date of Patent: Jun. 27, 2017

(54) SYSTEM COMPRISING A SECONDARY DEVICE WITH A PIEZOELECTRIC ACTUATOR WIRELESSLY SUPPLIED AND CONTROLLED BY A PRIMARY DEVICE

(75) Inventors: Thierry Bieler, Echichens (CH); Laurent Cardoletti, Villeneuve (CH); Christian Fleury, Cotterd (CH); Christian Koechli, Yvonnand (CH); Simon Tinguely, Lausanne (CH)

(73) Assignee: MICRO-BEAM SA, Yverdon-les-Bains (CH)

( * ) Notice: Subject to any disclaimer, the term of this patent is extended or adjusted under 35 U.S.C. 154(b) by 545 days.

(21) Appl. No.: 14/119,828

(22) PCT Filed: May 24, 2012

(86) PCT No.: PCT/EP2012/059776
§ 371 (c)(1),
(2), (4) Date: Feb. 12, 2014

(87) PCT Pub. No.: WO2012/160173
PCT Pub. Date: Nov. 29, 2012

(65) Prior Publication Data
US 2014/0213973 A1    Jul. 31, 2014

(30) Foreign Application Priority Data
May 25, 2011 (CH) .................. 897/11

(51) Int. Cl.
*H01L 41/08* (2006.01)
*H02N 2/00* (2006.01)
(Continued)

(52) U.S. Cl.
CPC ...... *H02N 2/0075* (2013.01); *A61M 5/14276* (2013.01); *A61M 39/22* (2013.01);
(Continued)

(58) Field of Classification Search
CPC ........... H01L 41/042; G01R 33/34084; A61B 5/0031; A61F 2/0036; A61F 2/0063
(Continued)

(56) References Cited

U.S. PATENT DOCUMENTS 6,015,386 A * 1/2000 Kensey et al. ............... 600/486
7,952,349 B2 * 5/2011 Huang et al. ................ 324/249
(Continued)

FOREIGN PATENT DOCUMENTS

DE   10 2006 041017 A1   7/2007
GB       2 440 571 A      2/2008
(Continued)

*Primary Examiner* — Thomas Dougherty
(74) *Attorney, Agent, or Firm* — Maschoff Brennan

(57) ABSTRACT

A system for contactless transmission of energy and control signals between a primary device and a secondary device. The primary device has a primary set with at least one primary coil and an electronic supply driver for supplying primary signals to the primary set of primary coils. A secondary device has a secondary set with at least one secondary coil, at least one piezoelectric actuator, and electronic components including a resonant circuit powered by the secondary set. The piezoelectric actuator is powered and controlled through the secondary set of secondary coils and the electronic components.

27 Claims, 15 Drawing Sheets

(51) Int. Cl.
*A61M 5/142* (2006.01)
*A61M 39/22* (2006.01)
*H02N 2/02* (2006.01)

(52) U.S. Cl.
CPC ............. *A61M 2205/0294* (2013.01); *A61M 2205/8243* (2013.01); *H02N 2/023* (2013.01); *H02N 2/025* (2013.01)

(58) Field of Classification Search
USPC .................... 310/314–319; 600/30, 421, 486
See application file for complete search history.

(56) References Cited

U.S. PATENT DOCUMENTS

| | | |
|---|---|---|
| 2003/0062794 A1 | 4/2003 | Scheible |
| 2009/0062886 A1* | 3/2009 | O'Handley et al. ............ 607/51 |
| 2009/0230777 A1* | 9/2009 | Baarman et al. ............. 307/104 |
| 2009/0259093 A1 | 10/2009 | Bhat |
| 2010/0052431 A1* | 3/2010 | Mita ............................ 307/104 |
| 2010/0133917 A1* | 6/2010 | Sekino et al. ................ 307/104 |
| 2011/0092948 A1 | 4/2011 | Shachar |
| 2012/0046520 A1 | 2/2012 | Augarten et al. |
| 2014/0163307 A1* | 6/2014 | Zilbershlag ..................... 600/16 |

FOREIGN PATENT DOCUMENTS

| | | |
|---|---|---|
| WO | 01/33061 A1 | 5/2001 |
| WO | 2006/138091 A1 | 12/2006 |

* cited by examiner

SYSTEM COMPRISING A SECONDARY DEVICE WITH A PIEZOELECTRIC ACTUATOR WIRELESSLY SUPPLIED AND CONTROLLED BY A PRIMARY DEVICE

The present invention relates to systems and devices for contactless transmission of energy and control signals between a primary device and a secondary device. The invention also relates to contactless transfer of energy and control between a first device such as, but not limited to, a control system outside a living body, and a secondary device such as but not limited to, a device suitable for insertion within a living body, such as a medical or diagnostic device, for example a drug dispensing device controlled from outside the body.

RELATED ART

US2012/0046520 discloses an implantable medical system for treating obesity. It comprises a piezoelectric actuator to move a fluid from reservoir to an inflatable portion of a gastric band. This system requires an implanted high voltage source to polarize the piezoelectric actuator.

US2009/0259093 relates to an artificial sphincter system comprising a piezoelectric element. In one embodiment, the piezoelectric actuator is powered by a power source outside the patient's body and the power is transmitted transcutaneously through an induction coil implanted in the patient's body. The induction coil is directly connected to the piezoelectric actuators and it is difficult to achieve the voltages which are required to drive the piezoelectric actuators without approaching the primary device very close to the secondary device and without supplying a high current to the coils of the primary device. Moreover, this solution requires a precise alignment of the primary device with the secondary device.

SUMMARY OF THE INVENTION

According to one aspect, the invention relates to a system comprising a primary device having on one side a primary set of coils, the primary set comprising at least one primary coil, and an electronic supply driver for supplying primary signals to said set of primary coils; and on the other side a secondary device comprising a secondary set with at least one secondary coil, at least one piezoelectric actuator, and electronic components including a resonant circuit powered by said secondary set, said piezoelectric actuator being powered and controlled through said secondary set of secondary coils and said electronic components.

The piezoelectric actuator and the electronic components in the secondary device are wirelessly powered by the primary device and don't require a battery. A power source may be in the primary device and power is transmitted wirelessly to the secondary device. The electronic components are controlled with the signals from the primary device.

The resonant circuit in the primary device increase the voltage level when the induced signal has the resonant frequency, so that a higher voltage may be obtained. Furthermore, this resonant circuit may be used to select which actuator should be activated if a plurality of actuators are provided.

The invention is particularly well adapted for medical systems to be implanted within the human body with no embedded control logic and which are controlled and supplied through contactless energy transfer through human skin and/or human tissues. The secondary device may be for example an implantable medical device. The piezoelectric actuator may control one valve. The primary device may be outside of the body. This solution allows wireless transfer of energy and control commands between an external primary device and an implanted secondary device, for opening and/or closing a valve.

The invention is also well adapted for non medical systems to be implanted within some kind of protected area with no embedded control logic and which shall be controlled and supplied though contactless energy transfer only.

The sense of displacement of the piezoelectric actuator is controlled by the phase and/or by the amplitude and/or by the frequency of at least one first signal supplied to at least one coil in said at least one primary coil.

In one embodiment, the sense of displacement of the piezoelectric actuator depends on the sense of a phase shift between one first current supplied to one first coil of said primary set and a second current supplied to one second coil of said primary set. In this example, a simple phase shift of the first current with regard to the second current will reverse the sense of displacement of the piezoelectric actuator.

In one embodiment, the sense of displacement of the piezoelectric actuator depends on the magnitude of a first current supplied to one primary coil. If the current (i1) is lower than a threshold, the piezoelectric actuator moves in one sense. If this current is higher than the threshold, the piezoelectric actuator moves in the opposite sense.

The secondary device comprise at least one resonant circuit arranged for delivering a signal with an amplitude higher than a threshold when at least one said primary current has a frequency corresponding to the resonance frequency of said resonant circuit, and for delivering a signal with an amplitude lower than said threshold when said frequency does not correspond to the resonance frequency of said resonant circuit. In this case, the secondary device moves said piezoelectric actuator in one first sense when said amplitude of said signal is higher than said threshold, and in the opposite sense when said amplitude of said signal is lower than said threshold. In this example, a simple frequency shift of the first current will reverse the sense of displacement of the piezoelectric actuator.

The secondary device may comprise only electronic components of the passive type. The secondary device used in the secondary device for detecting the sense of displacement from the amplitude, frequency or phase of the induced signals may be of the passive type. Therefore, the size, price, volume and power consumption of the secondary device can all be reduced.

In the present application, components are considered to be of "passive type" if they are not controlled by an external digital controller such as a microcontroller, a FPGA, a programmable element, or some complex logic circuitry. Resistors, capacitors, inductors and most two-terminal components are all components of a passive type. Because rectifying diodes are not controlled by an external signal, such as a signal from an embedded control electronic, they are also of passive type. According to the definition used in this application, other components which in their function are equivalent or could replace a passive component are also considered to be components of passive types. For example, the skilled person could use a transistor to replace a rectifying diode (which is a passive component); such a transistor would be considered to be of passive type, in particular if it is polarized by some resistors to act like a diode, or even this transistor it is controlled by a simple comparator for comparing the input and output voltage of the transistors in order to act like a diode. On the other end, transistor which would amplify a signal or whose state is controlled by a microcontroller, a FPGA, complex logic circuitry is not considered to be of passive type.

The primary set of coils in the primary device may comprise a plurality of primary coils. An electronic supply driver may be arranged to supply the primary coils with phase-shifted signals.

A primary device may comprise two sets of primary coils. The secondary set may comprise two secondary coils. The electronic supply driver may supply the primary sets of coils with two alternative phase voltages and/or currents shifted by +90° or −90° to generate in the secondary coils two induced voltages with a phase shift angle of 90° through contactless energy transfer, so as to control a displacement and/or a force on said piezoelectric actuator in forward or reverse direction.

The primary set may comprise three said primary coils, said electronic supply driver being arranged to supply said primary coils with three alternative phase voltages and/or currents shifted by +120° or −120° electrical degrees.

The electronic components of the passive type in the secondary device may comprise a rectifying diode and a capacitor for converting a signal received at said secondary coil in a DC voltage that supplies said piezoelectric actuator. A discharge resistor may be provided for discharging the capacitor when the contactless energy transfer is interrupted.

The electronic components of the passive type may build a resonant circuit with the secondary coil. A plurality of resonant circuits with a corresponding plurality of different resonant frequencies may be provided, so as to select different piezoelectric actuators depending on the frequency of the signal supplied to said primary coil. The primary coils may be supplied with a signal comprising a plurality of different frequencies selected so as to simultaneously drive a corresponding plurality of piezoelectric actuators. The primary device may also comprise a plurality of sets of coils, each set comprising a plurality of primary coils, said electronic supply driver being arranged for supplying different primary sets with different frequencies so as to simultaneously drive a corresponding plurality of piezoelectric actuators.

The primary device may comprise two primary sets of primary coils with two coils in each set, the coils in the first primary set being geometrically phase shifted with respect to the coils in the second primary set. An arrangement of two coils phase shifted by 90° is shown on FIG. 15.

The secondary device may comprise at least one secondary coil connected to an electronic component including a rectifying circuit, and at least one other secondary coil connected to an electronic component which does not include a rectifying circuit.

The secondary device may comprise a moving part with a magnet. A sensor may sense the displacement of said magnet. The primary device may further comprise tertiary coils for detecting displacements of a moving part in said secondary device.

The invention also relates to the primary device alone, and with the secondary device alone.

The invention further relates to a method for remotely powering and controlling a piezoelectric actuator, comprising:

supplying at least one current to at least one primary coil;
receiving on a secondary coil an induced signal induced by said first coil;
powering a piezoelectric actuator with said induced signal, so as to displace said piezoelectric actuator in a first sense;
modifying the amplitude and/or phase and/or frequency of said at least one current supplied to said at least one primary coil, so as to induce a different induced signal on said secondary coil and to displace said piezoelectric actuator in a second sense.

According to another, possibly independent aspect, the invention further relates to a system comprising:

A primary device having a first primary set with at least one primary coil, a second primary set with at least one primary coil, the coils in said first primary set being phase shifted with respect to the coils in said second primary set, said primary device further comprising an electronic supply driver for supplying first primary signals to said first primary set of primary coils, and for supplying second, electrically phase-shifted second primary signals to said second primary set of primary coils, A secondary device comprising a secondary set with at least one secondary coil, at least one piezoelectric actuator, and electronic components powered by said secondary set, said piezoelectric actuator being powered and controlled through said secondary set of secondary coils and said electronic components.

The use of phase shifted coils in the primary device and of phase-shifted signals supplied to those coils generate a rotating magnetic field in the coils of the secondary device. Therefore, the coils of the primary device can be superimposed over the coils of the secondary device at any angle, without any need for alignment, and without any need for spacing the two coils.

The primary device could comprise two orthogonal sets of coils and an electrical phase shift between the supply signals provided to those two different sets of 90°. In one embodiment, the primary device comprises n=3 sets of primary coils with a geometrical phase-shift of 120° and an electrical phase-shift between the signals supplied to those three sets of 120°.

Traditional setup would implement the contactless energy transfer and have embedded control electronic for the control of the actuators. The proposed solutions allow reducing for the embedded parts: the complexity, the size/volume, the cost as well as the risk of failure. The use of a rotating field for the contactless energy transfer allows for a positioning of the primary device which is independent or nearly independent from the positioning of the secondary device, at any angle α. Moreover, a plurality of phases in the secondary device may be used for controlling a multiphase ultrasonic actuator in the secondary device. The use of contactless energy transfer combined with rectifying circuitry and discharge resistance allows controlling piezoelectric components with DC voltage sequences. Multiplying this scheme for different electrode connections and using different resonant frequencies to be able to select the actuator parts to be activated is advantageous.

SHORT DESCRIPTION OF THE FIGURES

The present invention will better understood with the detailed description of some possible embodiments illustrated by the figures in which:

FIG. 1 shows a system with a primary device and a secondary device with a piezoelectric actuator controlled and power supplied by the primary device.

FIG. 2 schematically illustrates a simple coil scheme for transmitting energy between a first coil and a second coil.

Figure 11:
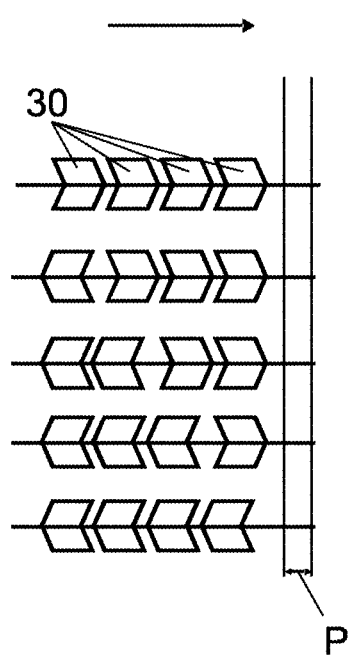
Figure 12:
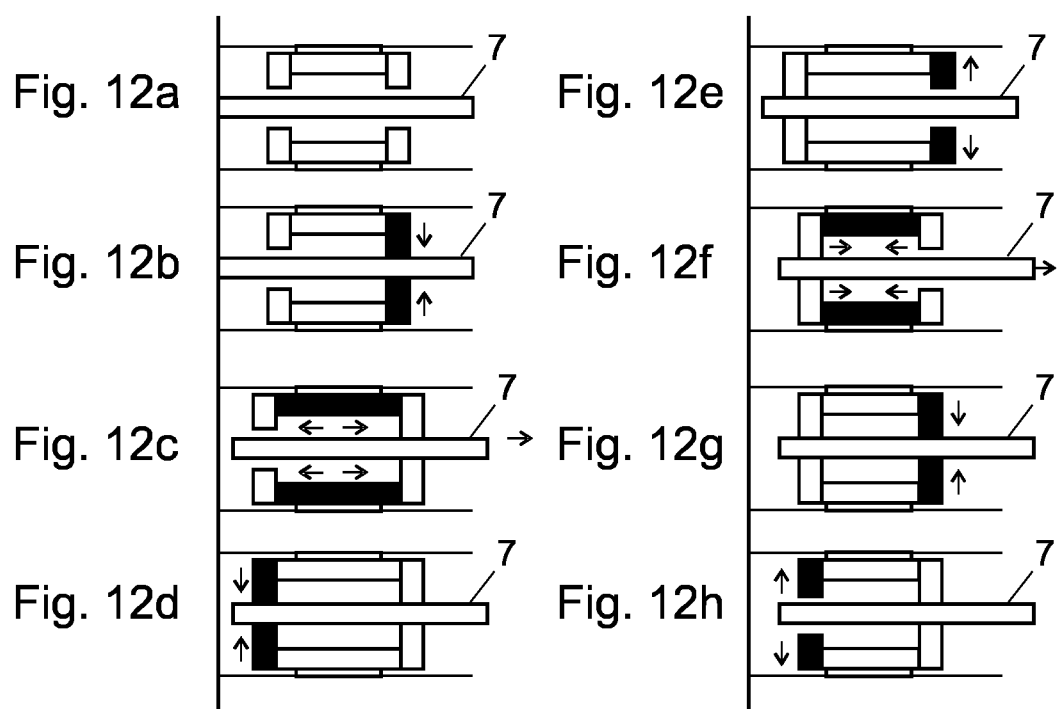

FIG. 11 schematically illustrates an actuator comprising several piezoelectric elements and allowing a synchronous forward motion and an asynchronous backward motion.

FIGS. 12a to 12h schematically illustrates 6 steps of the actuation process of a piezoelectric inchworm motor.

Figure 13:
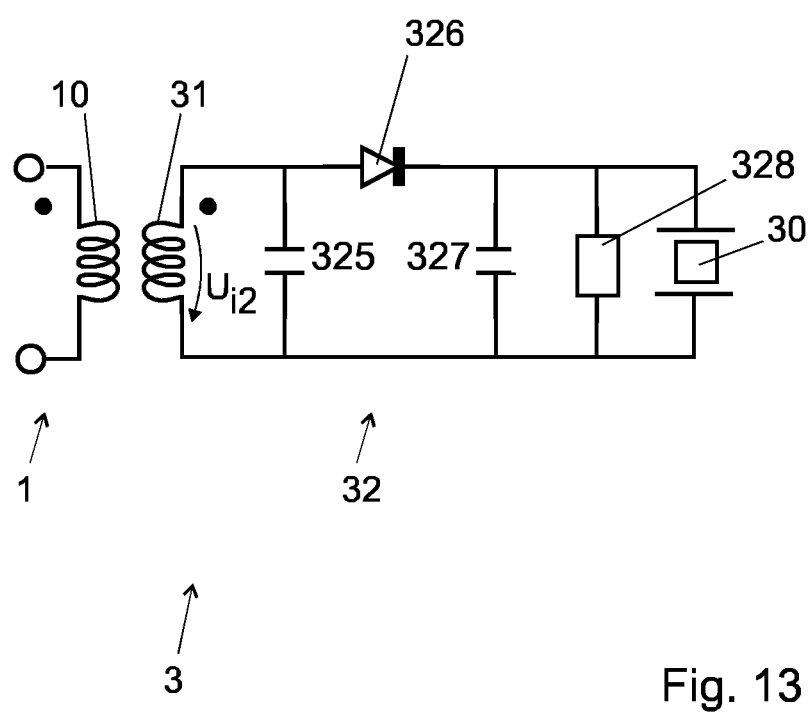

FIG. 13 illustrates a circuit for the secondary device comprising one secondary coil, a resonant capacitor, an unipolar rectifier with a diode and a second capacitor, a discharge resistance and a piezoelectric actuator.

Figure 14:
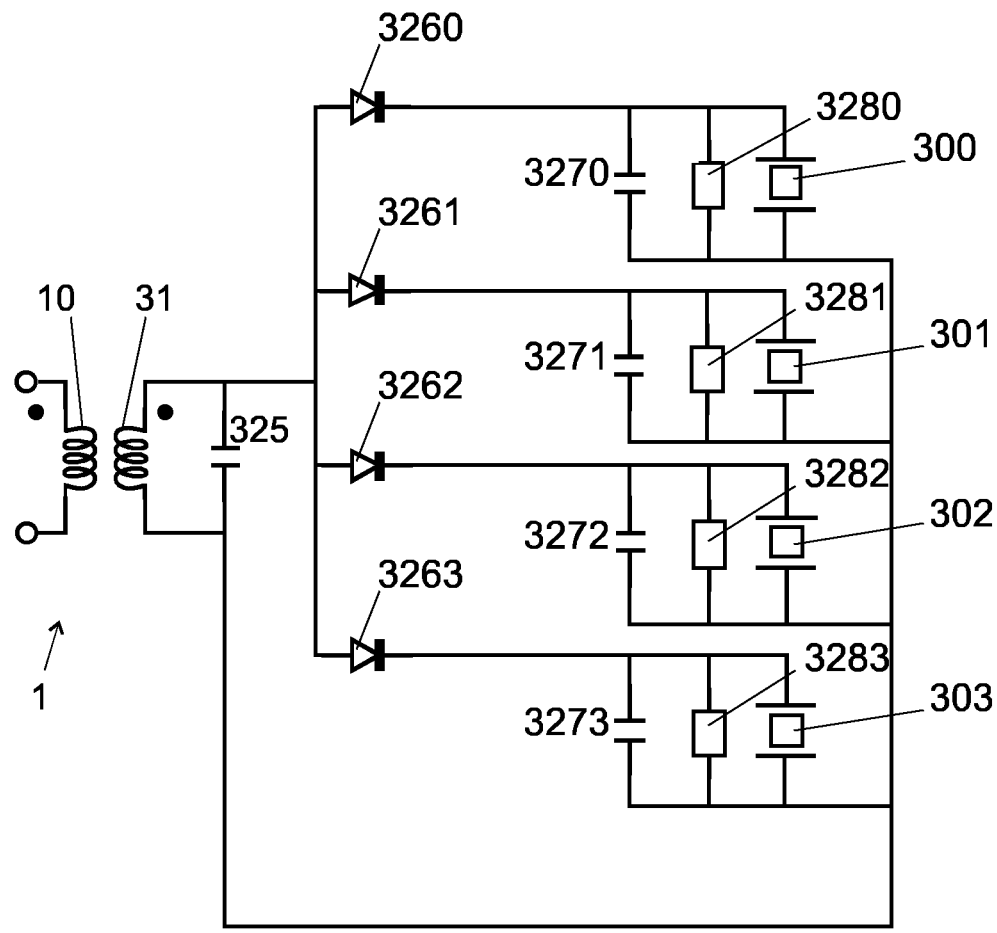

FIG. 14 illustrates an example of circuit for the secondary device comprising four independent rectifiers, four different discharge resistors and four piezoelectric actuators.

Figure 15:
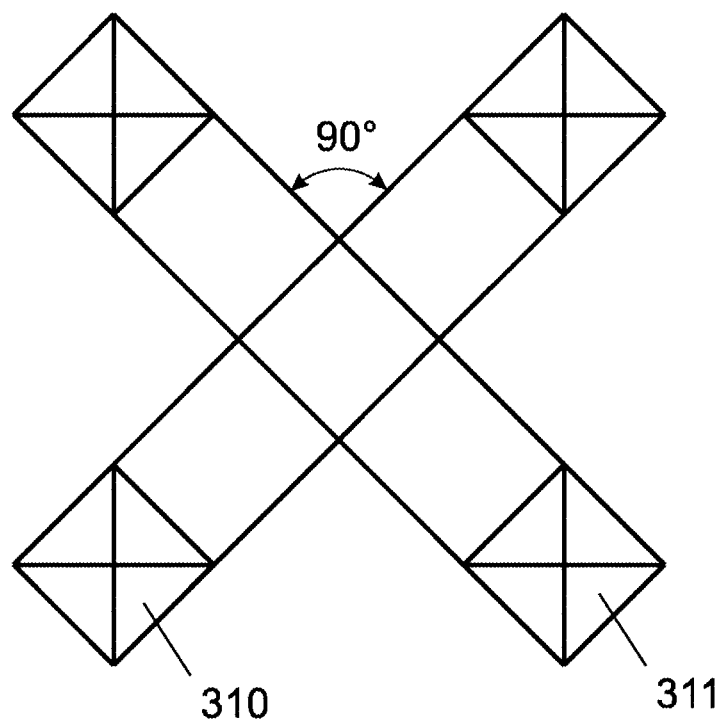

FIG. 15 is a top view over two coils physically shifted by 90°.

Figure 16:
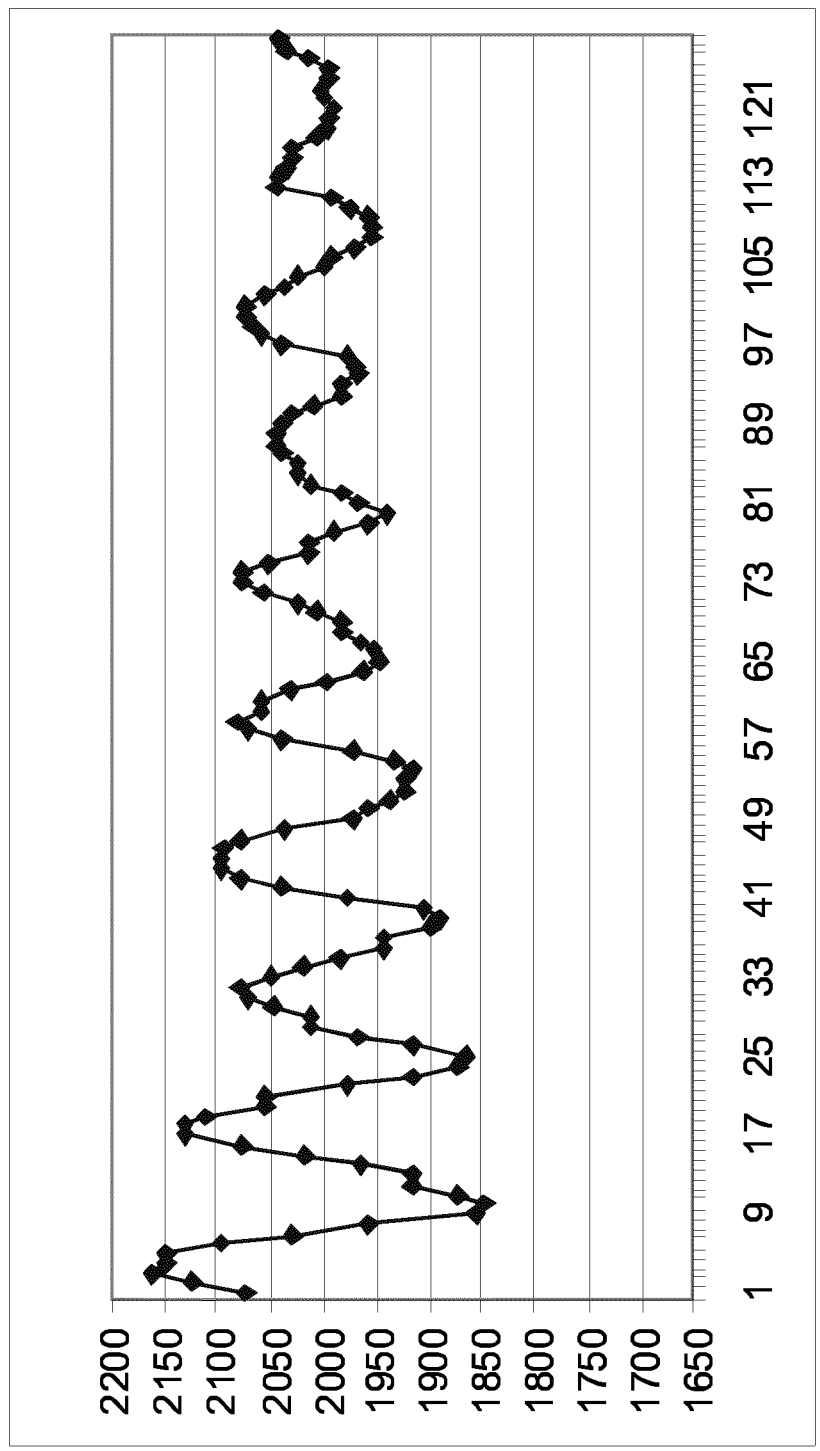

FIG. 16 is a waveform illustrating the induced voltage in one tertiary coil produced by the interruption of the secondary current following a supply interruption of the primary coil sets.

DETAILED DESCRIPTION

Figure 1:
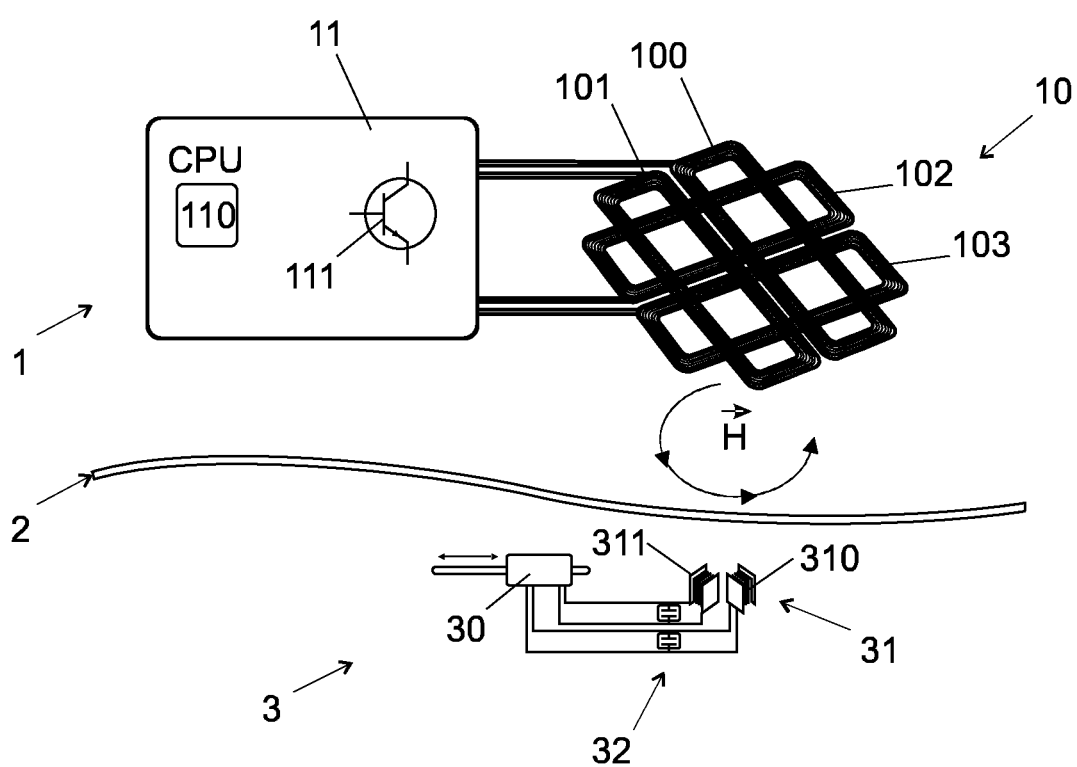

FIG. 1 illustrates a system according to one possible embodiment of the invention. The system comprises a primary device 1 and a secondary device 3 with an actuator 30. The secondary device 3 could be an implant, for example an implanted drug delivery device with a valve controlled by the actuator, while the primary device 1 is a control device for contactless power supplying the secondary device and controlling the motion of the actuator. In this example, 2 is the skin separating the primary device from the secondary device.

In this example, the actuator 30 is a two phases bidirectional piezoelectric actuator supplied with a contactless energy transfer set up robust against primary/secondary alignment issues thanks to the use of a rotating field. An electronic control and supply driver 11 supplies two primary coil sets 10 with two alternative phase voltages and/or currents. The first coil set comprises two coils 100, 101 while the second coil set comprises two coils 102,103.

The two coil sets are physically shifted by 90°. The driver 11 generates voltages u1 and currents i1 which are supplied to the two coil sets. Example of suitable waveforms for the voltages and currents are shown on FIG. 9. In a preferred embodiments, the currents i1 and voltages u1 supplied to the two sets are shifted by +90° to generate a displacement and/or a force on the embedded piezoelectric actuator 30 in forward direction, or shifted by −90° to generate a displacement and or a force on the embedded piezoelectric actuator in reverse direction.

Figure 9:
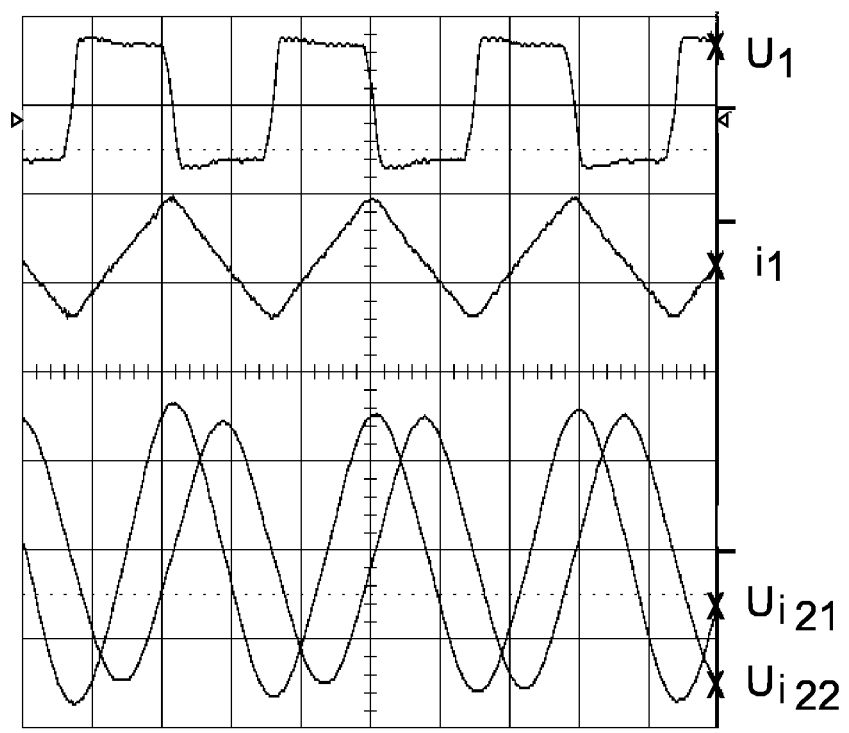
FIG. 9 illustrates a primary supply voltage u1 supplied to two primary coils sets with a 90° phase shift, the primary supply current i1, and the induced secondary voltage waveforms $u_{i21}$ and $u_{i22}$ in two secondary coils shifted by 90°.

The secondary device 3 comprises an embedded secondary coil sets 31 with two orthogonal coils 310 and 311, as well as few embedded passive electronic components 32, such as for example resonant capacitors. Having the piezo actuator resonant frequency close to the secondary coil electrical resonant frequency allow to optimize the efficiency of the energy transmission. When a voltage is induced in the secondary coil set 31 by the primary coil sets 10, the electronic components 32 supply the piezoelectric actuator with 2 alternative phase voltages and/or currents shifted by +90° or −90°. Example of the induced voltages u21 and u22 in the two secondary coils are shown in FIG. 9.

Figure 2:
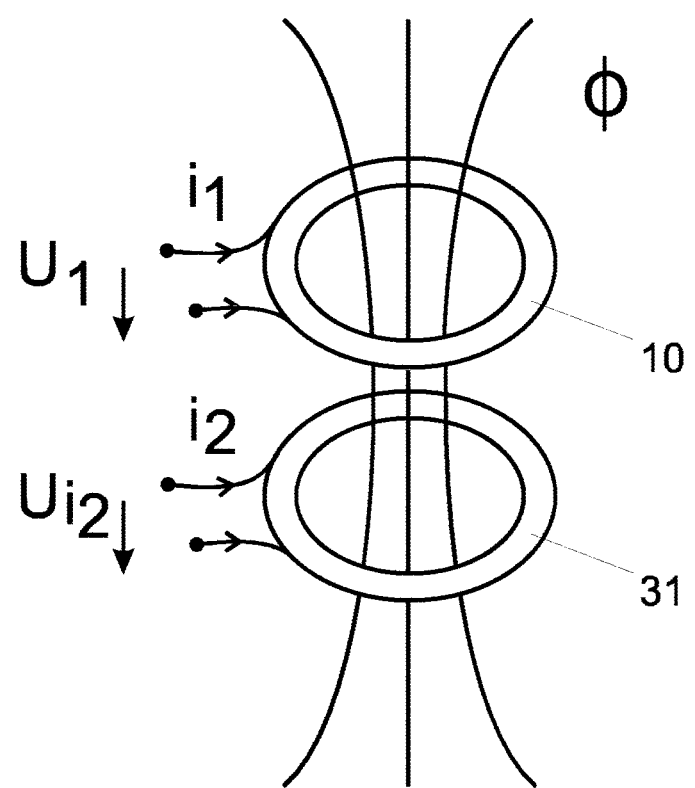

The rotating electromagnetic field H generated by the system presented in FIG. 1 is robust to misalignment between primary and secondary coils. However, more simple coils scheme that do not generate a rotating field could also be used for transmitting power and control between a primary and a secondary device, as illustrated in FIG. 2. In this simple setting, the primary device comprises one primary coil 10 and the secondary device comprises one secondary coil 31. When a primary current i1 or voltage u1 is supplied to the primary coil 10, an electromagnetic field φ is generated that induces a secondary voltage u2 and current i2 in the secondary coil 31. This induced secondary current/voltage could be used for supplying and controlling a piezoelectric actuator over a suitable electronic circuit.

Figures 3A, 3B:
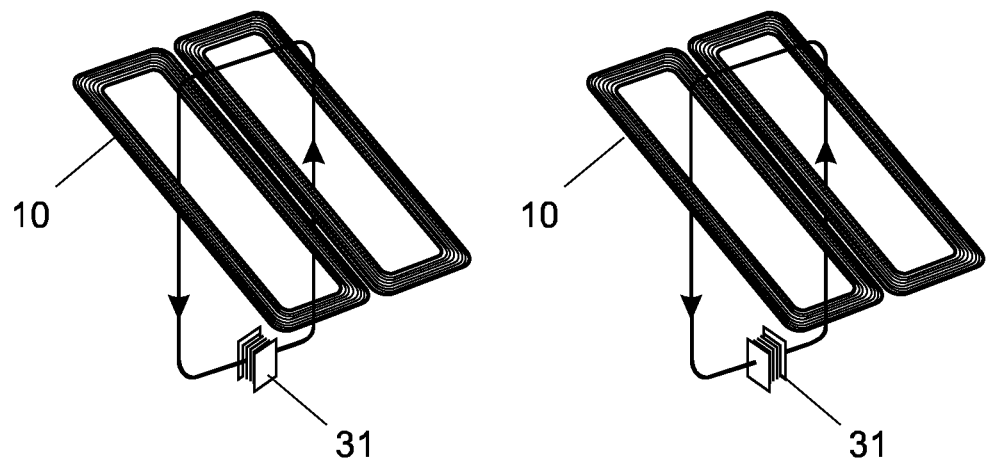
FIGS. 3a and 3b illustrates the coupling between primary coils and secondary coils in function of the relative angular position α.

Some primary and secondary coils schemes allow a variation of the coupling between primary coil(s) and secondary coil(s) in function of the relative angular position α between secondary and primary coils, $L_{12}=f(\alpha)$ as shown in FIGS. 3a and 3. In FIG. 3a, the primary and secondary coil set 31 are physically phase shifted by an angle α=90°; the coupling and mutual inductance $L_{12}$ between the coil set 10 and the coil set 31 are zero. In FIG. 3b, the primary and secondary coil set 31 are physically phase shifted by an angle α=0°; the coupling and mutual inductance $L_{12}$ between the coil set 10 and the coil set 31 are maximal $L_{12}=\hat{L}_{12}$ More generally, for demonstration purpose, the variation of the coupling and/or mutual inductance in function of the angle α is assumed to be a cosine function:

$$L_{12}=\hat{L}_{12}\cos(\alpha)$$

Figure 4:
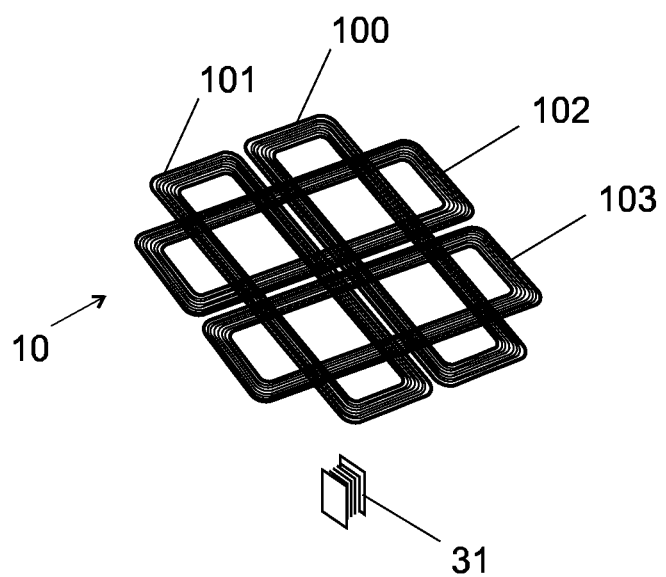
FIG. 4 illustrates the coupling in a scheme with two sets of primary coils and one secondary coil.

Two phase-shifted sets of primary coil(s) can be used to produce a rotating magnetic field, similar to the magnetic field in an AC induction motor. A scheme with two sets of coils 100-101 and 102-103 in the primary device 1 and one set of coil 31 in the secondary device 3 is shown in FIG. 4.

The mutual inductances between the two primary sets of coils and the secondary coil can be approximated as cosines:

$$L_{1a2}=\hat{L}_{12}\cos(\alpha), L_{1b2}=\hat{L}_{12}\cos(\alpha+\theta_g)$$

where $L_{1a2}$ is the mutual inductance between the first set of primary coils and the secondary coil, $L_{1b2}$ is the mutual inductance between the first set of primary coils and the secondary coil, and $$\theta_g = \frac{\pi}{2}$$

is the phase shift angle between the two sets of primary coils

The two sets of primary coils 100-101 and 102-103 could be supplied with sinusoidal currents $i_{1a}$ respectively $i_{1b}$:

$$i_{1a} = \hat{I}_1 \cdot \sin(\omega t)$$

$$i_{1b} = \hat{I}_1 \cdot \sin(\omega t + \beta)$$

where $$\beta = \frac{\pi}{2}$$

is the electrical phase shift angle between the sinusoidal currents supplying both set of primary coils.

The induced voltage $u_{12}$ in the secondary coil 31 is given by the following general relationship:

$$u_{i2} = L_{1a2} \cdot \frac{d i_{1a}}{dt} + L_{1b2} \cdot \frac{d i_{1b}}{dt}$$

$$= \hat{L}_{12} \cdot \hat{I}_1 \cdot \omega \cdot (\cos(\alpha) \cdot \cos(\omega t) + \cos(\alpha + \theta_g)\cos(\omega t + \beta))$$

with $$\cos(\omega t) \cdot \cos(\alpha) = \frac{1}{2}\cos(\omega t + \alpha) + \frac{1}{2}\cos(\omega t - \beta)$$

and with $$\cos(\omega t + \beta)\cos(\alpha + \theta_g) = \frac{1}{2}\cos(\omega t + \beta + \alpha + \theta_g) + \frac{1}{2}\cos(\omega t + \beta - \alpha - \theta_g).$$

If $\theta_g = \frac{\pi}{2}$, $\beta = \frac{\pi}{2}$, we have:

$$u_{i2} = L_{1a2} \cdot \frac{d i_{1a}}{dt} + L_{1b2} \cdot \frac{d i_{1b}}{dt}$$

$$= \hat{L}_{12} \cdot \hat{I}_1 \cdot \omega \cdot \left(\cos(\alpha) \cdot \cos(\omega t) + \cos\left(\alpha + \frac{\pi}{2}\right)\cos\left(\omega t + \frac{\pi}{2}\right)\right)$$

with $$\cos(\omega t) \cdot \cos(\alpha) = \frac{1}{2}\cos(\omega t + \alpha) + \frac{1}{2}\cos(\omega t - \alpha)$$

and with $$\cos\left(\omega t + \frac{\pi}{2}\right)\cos\left(\alpha + \frac{\pi}{2}\right) = \frac{1}{2}\cos(\omega t + \alpha + \pi) + \frac{1}{2}\cos(\omega t - \alpha)$$

$$\cos\left(\omega t + \frac{\pi}{2}\right)\cos\left(\alpha + \frac{\pi}{2}\right) = -\frac{1}{2}\cos(\omega t + \alpha) + \frac{1}{2}\cos(\omega t - \alpha)$$

We finally obtain:

$$u_{i2} = \hat{L}_{12} \cdot \hat{I}_1 \cdot \omega \cdot (\cos(\omega t - \alpha))$$

Therefore, the induced voltage $u_{i2}$ in the secondary coil 31 is a cosinusoidal function with a magnitude independent from the angle $\alpha$.

Figure 5:
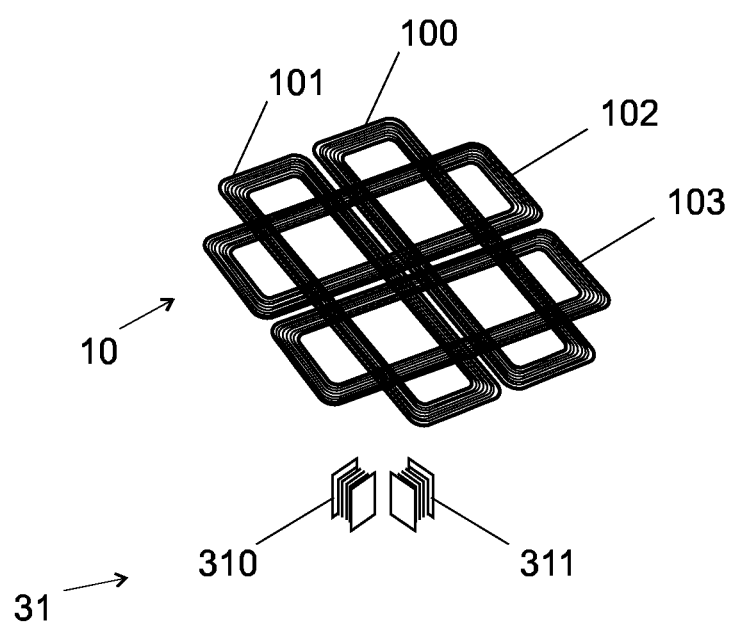
FIG. 5 illustrates the coupling in a scheme with two sets of primary coils and two secondary coils.

FIG. 5 illustrates a scheme with a first secondary coil 310 with angle $\alpha=0$ and a second secondary coil 311 with an angle $$\alpha = \frac{\pi}{2}.$$

This arrangement create two cosinusoidal induced voltages $u_{i2a}$ and $u_{i2b}$ with a phase shift of $$\frac{\pi}{2}$$

between them:

$$u_{i2a} = \hat{L}_{12} \cdot \hat{I}_1 \cdot \omega \cdot \cos(\omega t)$$

$$u_{i2b} = \hat{L}_{12} \cdot \hat{I}_1 \cdot \omega \cdot \cos\left(\omega t - \frac{\pi}{2}\right)$$

The generation of a rotating field requires at the primary level at least two phases, but a set of three phases shifted by 120° with current supply shifted by 120° would also allow to generate a rotating field. This rotating field generated by n different sets of coils in the primary device could be used in combination with a single set of secondary coils in the secondary device, or with two phase systems having two sets of secondary coils in the secondary device, or with a triphasic system having three sets of secondary coils in the secondary device, etc.

Having two secondary coils mechanically shifted by 90° allows for example to generate in two secondary coils two induced voltages with a phase shift angle of 90° electrical degrees through contactless energy transfer. Having three secondary coils mechanically shifted by 120° allows for example to generate at the secondary level three induced voltages with a phase shift angle of 0°, 120° and 240° (a demonstration similar to the one of the 2 phases scheme can be conducted). More generally, the use of n phases in the primary device allows to generate a rotating field if the n phases are supplied with suitably phase—shifted signals. Once we have a rotating field, the number of secondary coils 31 and their repartition angle allow either to supply a single monophasic actuator in the secondary device, or a plurality of actuators, or one or a plurality of multiphase actuators with electrical phase shift angle selectable at will. It is also possible to use four phases shifted by 0°, 45°, 90° et 135° or by 0°, −45°, −90° and −135°; for four phases shifted by 0°, 90°, 15° and 105°, or by 0°, −90°, −15° and −105°; or four phases shifted by 0°, 90°, 25° and 115°, or by 0°, −90°, −25° and −115°. More generally, the secondary can have n phases, n>=2.

Figure 6:
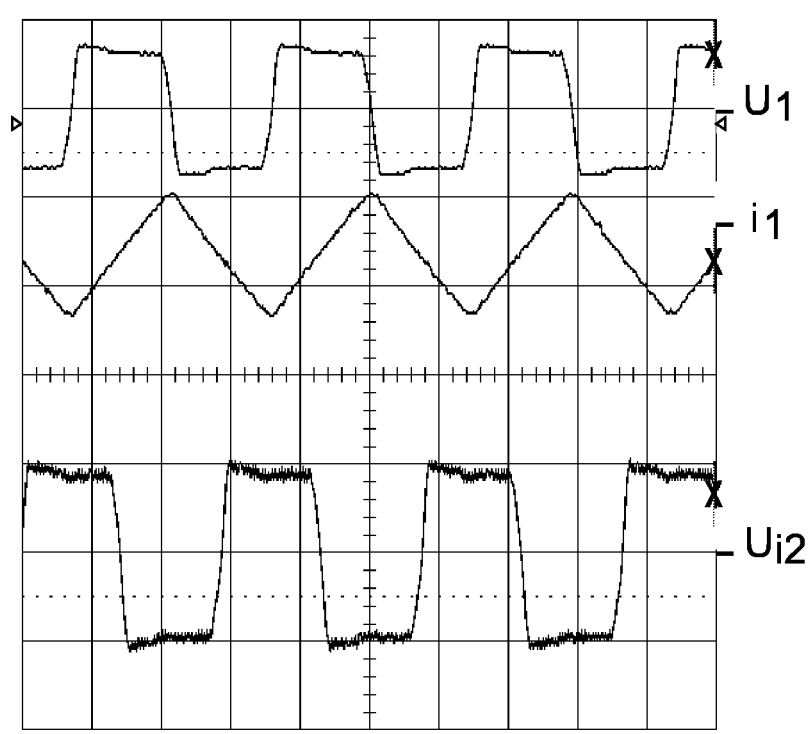
FIG. 6 illustrates the primary supply voltage u1, the primary supply current i1 and the corresponding induced secondary voltage $u_{i2}$.

To implement a contactless energy transfer, the primary coils are preferably supplied with alternative current and/or voltage with a frequency in general in the range of 1 kHz to 1 MHz. Sinusoidal waveform have been considered for demonstration purpose. Other waveform like square voltage u1 on primary coil can advantageously be used, as shown on FIG. 6, and can be produced for example with a four transistors H power bridge. In the latter case, the induced voltage $U_{i2} = L_{12} di_1/dt$ in each secondary coil is a square waveform too.

Figure 7:
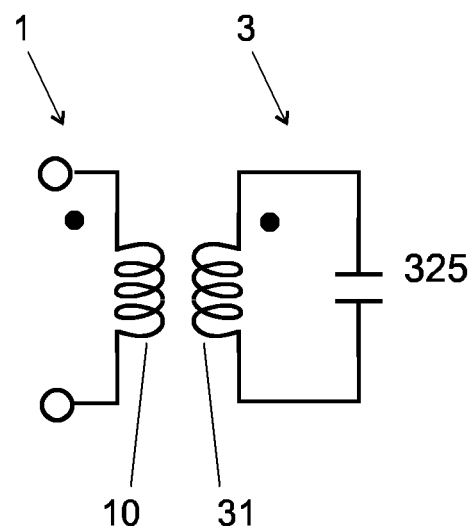
FIG. 7 illustrates a resonant circuit for the secondary device.
Figure 8:
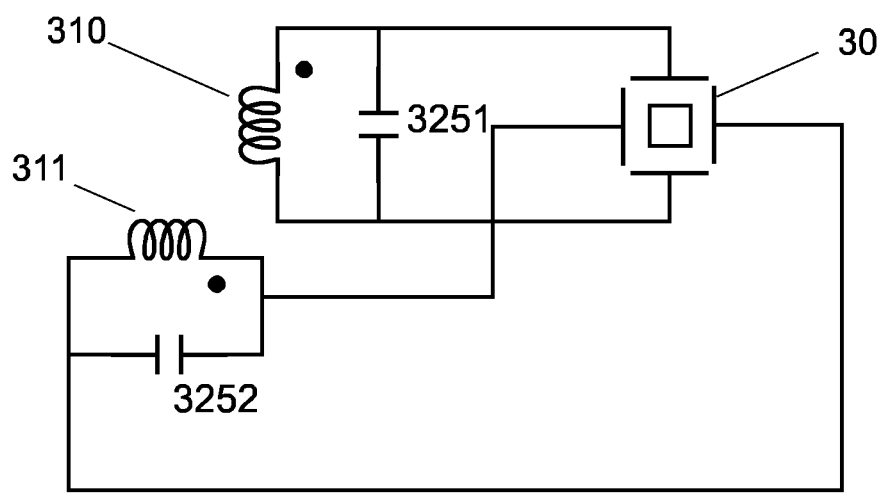
FIG. 8 illustrates a secondary device having two secondary coils physically shifted by 90° to supply an actuator with two phases.

FIGS. 7 and 8 show example of electronic arrangements for the secondary device 3, both based on a resonant circuit. FIG. 7 is an embodiment with a single secondary coil set 31 and one resonant capacitor 325, and FIG. 8 shows an example with two secondary coil sets 310, 311 and two corresponding resonant capacitors 3251 respectively 3252. The resonant capacitor 325, 3251, 3252 build with the-matched coil 31, 310, resp. 311 a LC filter with a given resonant frequency. The use of resonant circuitry at the secondary level allows to increase the induced voltage magnitude and to obtain more sinusoidal induced voltages at the secondary level, as shown on FIG. 9.

The example previously described in relation with FIG. 1 uses a two phases bidirectional piezoelectric actuator. However, the secondary device could use other types of piezoelectric actuators 30 such as for example a stick and slip piezoelectric actuator as illustrated in FIG. 10a. In this example, the piezoelectric actuators 30 are used as tiltable legs for sticking/pushing a part 7 to the right of the Figure when the piezoelectric actuators are moved in a first direction (second line of FIG. 10a), and for letting this part 7 slip above the legs when the piezoelectric actuators are moved in the opposite direction (third line), so as to displace the part by a pitch P at each cycle. The corresponding applied voltage corresponding to each step $u_{i2}$ is schematically illustrated next to this step.

Figure 10B:
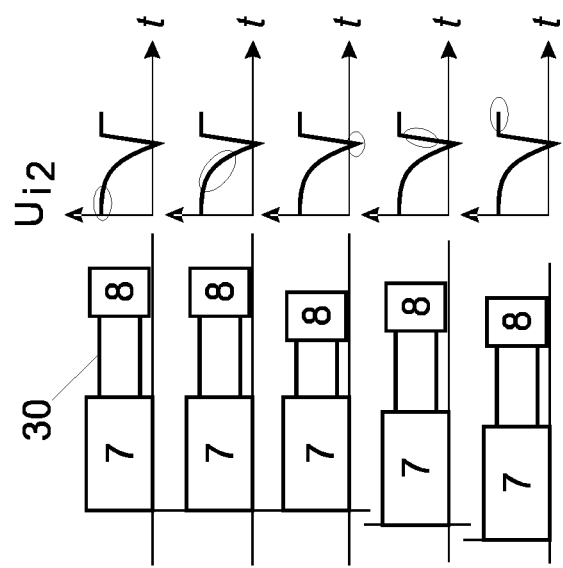
FIG. 10b is a schematic illustration of the displacement of a stick actuated by a piezoelectric element in function of the applied voltage.
Figure 10A:
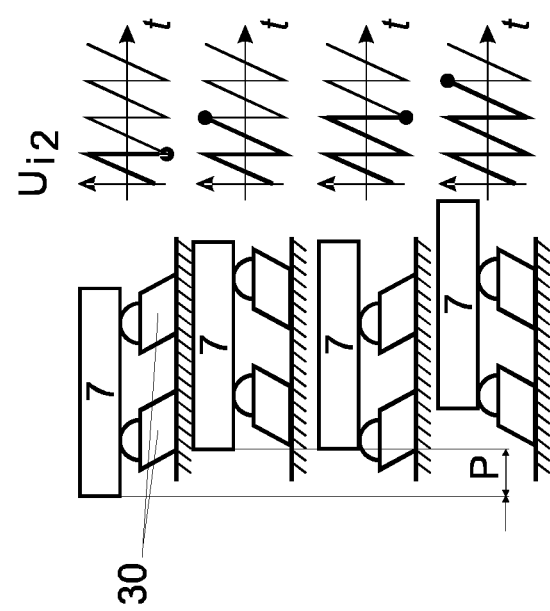
FIG. 10a is a schematic illustration of the displacement of a stick actuated by a piezoelectric element in function of the applied voltage.

FIG. 10b shows another embodiment where the piezoelectric actuators 30 are used as impact drive actuator to move a part 7; 8 is a weight. The process starts in the second line. In the third line, the piezoelectric element is slowly contracted with a slowly decreasing voltage $u_{i2}$, resulting in a displacement of the weight 8. In the fourth and fifth lines, the piezoelectric element is suddenly expanded, resulting in a fast displacement of the part 7.

FIG. 11 shows another embodiment where a plurality of piezoelectric actuators 30 controllable in a shear mode PZT are used for producing a synchronous forward motion, and an asynchronous backward motion.

FIGS. 12a to 12h show consecutive steps of displacement of another embodiment of piezoelectric actuator used as an inchworm motor. FIG. 12a shows the state when all piezoelectric actuators are relaxed and FIG. 12b shows the initialization process. FIGS. 12c to 12h show 6 consecutive steps of displacement of the part 7.

The piezoelectric actuators could also be used in other types of secondary devices, including without limitations flexure-guided piezoelectric actuators; direct-drive piezoelectric actuators; flexure-guided lever mechanisms that mechanically amplify the motion of an integrated piezoelectric ceramic; etc. They can be used for controlling a valve or an opening for delivering a drug, opening or closing a tube etc.

FIG. 13 shows an embodiment of secondary device 3 comprising some electronic components 32 to supply a piezoelectric actuator 30 with a DC voltage through contactless energy transfer. The contactless energy transfer can advantageously be realized using the above mentioned rotating field principle (to be less sensitive to alignment issues) or by using more simple coils scheme like in FIG. 2. The capacitor 325 builds with the secondary coil 325 a resonant LC filter. A rectifying diode 326 allows charging the capacitor 327 with a DC voltage that will supply the piezoelectric actuator 30 when primary coil 10 induces a voltage $u_{i2}$ in the secondary coil 31. The discharge resistance 328 will discharge the capacitor 327 when the contactless energy transfer is interrupted.

FIG. 14 shows an embodiment of secondary device 3 comprising some electronic components 32 to supply a plurality of piezoelectric actuators 300 to 303 with a DC voltage through contactless energy transfer. The contactless energy transfer can be realized using the above mentioned rotating field principle or by using more simple coils scheme not creating a rotating field like in FIG. 2. 325 is a resonant capacitor building a resonant filter with the secondary coil 31. Rectifying diodes 3260 to 3263 allow charging each of the capacitors 3270 to 3273 with DC voltages that will supply their corresponding piezoelectric actuators 300 to 303 when the energy transfer is activated. The discharge resistances 3280 to 3283 will discharge their corresponding capacitors when the contactless energy transfer is interrupted. The values of the capacitors 3270 to 3273 and/or the values of the resistors 3280 to 3283 might be different, thus resulting in different time constants for each of the piezoelectric actuators 30 and in different durations of actuation and time to recover their initial state when the energy transfer is interrupted.

In a further embodiment (not shown), different secondary coils with different resonant electrical frequencies allows selecting the piezoelectric actuator to be supplied by changing the frequency of the supply signal applied to the primary coil/coils. For example, a plurality of secondary circuits similar to the circuit of FIG. 13 may be used, each circuit having a different resonant frequency. Such an arrangement may be used for example to drive an Inchworm actuator like the actuator of FIG. 12. To supply at the same time more than one piezoelectric actuator with different resonant electrical frequencies, the primary coil/coils can be supplied with a voltage/current comprising more than one frequency component corresponding to the desired different resonant electrical frequencies. Another solution to supply at the same time more than one piezoelectric actuator in the secondary device 3 with different resonant electrical frequencies is to supply different primary coil/coils set with a voltage/current component with one of said different resonant electrical frequencies.

The presented invention may be used for building simple systems with only one type of piezoelectric actuator, but also for building complex system with several types of piezoelectric actuators. For instance the two phases bidirectional piezoelectric actuator of FIG. 1 can be combined with other types of piezoelectric actuators using a rectifying circuitry (as illustrated for example on FIG. 13 and/or FIG. 14) to implement annex functionalities (locking/unlocking functions, valve control, . . . ). The supply frequency can be used to select the piezoelectric elements that will be activated in function of the system resonant frequencies. Multiple set of primary coils can also be used to activate several piezoelectric actuators at the same time at different resonant frequencies. Each resonant sub system can then act like a pass band filter.

All the solutions described so far are preferably implemented with an open loop concept: the piezoelectric actuators are supplied and controlled through the powering of the contactless energy transfer means without verifying if the target motion/function has been successfully realized.

It is however possible to build a closed system and to add feed back means using either contactless information transfer or a system allowing to measure a feedback at distance and to verify if the target motion has been realized. In one embodiment a magnet is provided on the moving part in the secondary device, while a sensor or a plurality of sensors are provided in the primary device to measure the magnet displacement (rotation and/or linear displacement). In another embodiment, a coil with a resonant circuitry in provided on the mobile part in the secondary device. This coil can be excited by the primary coils: measuring in the primary device the magnetic flow produced by those tertiary coils can then be used to measure for instance a coupling change. FIG. 16 illustrates an example of induced voltage in one tertiary coil produced by the interruption of the secondary current when the primary current has been interrupted. By measuring in each tertiary coil a signal like the one shown on FIG. 16, the ratio of the signal magnitude between tertiary coils can be used to measure a rotation; other arrangements of listening coils can be used to measure a translation motion. A sweep in frequency can be used to monitor a resonant frequency change of the coil with a resonant circuitry on the mobile part if one the parameter of this coil changes with a displacement (inductance and/or capacitor value can be displacement dependant).

Those embodiments including feedback means are preferably still consistent with the principle of having no control electronic logic embedded in the secondary device and to use only embedded electronic components of passive type in the secondary device. The electronic control logic for controlling the piezoelectric actuators remains in the primary device and each piezoelectric actuator is remotely supplied and controlled only through the primary device.

Coils used in this invention can be built with or without electromagnetic core. The use of ferrite core may allow increasing the coupling between coils.

The shape of the coils presented in this invention have to be considered as examples. Using other coil shape and/or other coil assembly would also allow implementing the invention.

REFERENCE NUMBERS

1 Primary device
10 Set of coils of the primary device
100,101 Coils in the primary set
102,103 Coils in the primary set
11 Electronic supply driver
110 Microcontroller (CPU)
111 Set of transistors
2 Skin
3 Secondary device
30 Piezoelectric actuator
300-303 Piezoelectric actuators
31 Secondary coils
310 Coils in the secondary set of coils
311 Coils in the secondary set of coils
32 Electronic components of the second device
325 Resonant capacitor
326 Rectifying diode
3260-3263 Rectifying diodes
327 Capacitor
3270-3273 Resonant capacitors
328 Discharge resistor
3280-3283 Discharge resistors
7 Part
8 Weight

The invention claimed is:

1. A system comprising:
an implantable medical or non-medical device comprising at least one piezoelectric actuator; and
an external device having a primary set with at least one primary coil and an electronic supply driver for supplying primary signals to said primary set for wireless transfer of energy and control commands between said external device and said implantable device for remote power and control of said piezoelectric actuator;
said implantable device including a resonant circuit comprising a secondary set with at least one secondary coil, a capacitor and electronic components powered by said secondary set, said piezoelectric actuator being powered and controlled through said secondary set of secondary coils and said electronic components;
wherein a direction of displacement of said piezoelectric actuator depends on the phase and/or on the amplitude and/or frequency of at least one first signal supplied to at least one coil in said at least one primary set;
wherein the direction of displacement of said piezoelectric actuator depends on a direction of a phase shift between one first current supplied to one first coil of said primary set and a second current supplied to one second coil of said primary set.

2. The system of claim 1, arranged for moving said piezoelectric actuator in a first direction when one first current supplied to one first coil is lower than a threshold, and for moving said piezoelectric actuator in the opposite direction when said first current supplied to said first coil is higher than said threshold.

3. The system of claim 1, wherein said resonant circuit is arranged for moving said piezoelectric actuator in a first direction when at least one said primary signal has a frequency corresponding to the resonance frequency of said resonant circuit, and for moving said piezoelectric actuator in the opposite direction when the frequency of said signal does not correspond to the resonance frequency of said resonant circuit.

4. The system of claim 1, further comprising:
one rectifier comprising one diode and one capacitor; and
one discharge resistor in parallel with said piezoelectric actuator.

5. The system of claim 1, wherein all electronic components are of passive type.

6. The system of claim 1, said primary set comprising a plurality of said primary coils, said electronic supply driver being arranged to supply said primary coils with phase-shifted signals.

7. The system of claim 6, said external device comprising two orthogonal primary sets of coils, said electronic supply driver being arranged to supply said primary sets with two signals electrically phase-shifted by +90° or −90.

8. The system of claim 6, said primary set comprising three physically phase shifted primary sets of coils, said electronic supply driver being arranged to supply said primary sets of coils with three alternative phase voltages and/or currents shifted by +120° or −120° electrical degrees.

9. The system of claim 6, said implantable device comprising a single secondary coil for actuating a single actuator.

10. The system of one of the claim 1, said implantable device comprising two orthogonal secondary coils in which two induced voltages with a phase shift angle of +90° or −90° are induced.

11. The system of claim 1, said implantable device comprising n phase-shifted secondary coils in which a plurality of phase shifted induced voltages are induced.

12. The system of claim 10, said implantable device comprising a plurality of actuators individually commanded by signals induced in different secondary coils or pairs of secondary coils.

13. The system of claim 1, said secondary set comprising two orthogonal secondary coils in which two induced voltages with a phase shift angle of +90° or −90° are induced, so as to move said piezoelectric actuator in a direction depending on the direction of said phase shift.

14. The system of claim 1, said implantable device comprising a plurality of independently selectable actuators.

15. The system of claim 14, said implantable device comprising a plurality of resonant circuits for independently actuating said piezoelectric actuators, wherein the selected actuator depends on the frequency of the induced signal.

16. The system of claim 14, comprising one secondary coil, one resonant capacitor building with said secondary coil a resonant circuit, a plurality of capacitors, each of said capacitors being in parallel with one said piezoelectric actuator, and a plurality of discharge resistors, each of said capacitors being in parallel with one said piezoelectric actuator.

17. The system of claim 16, wherein the values of the different capacitors and/or the values of the discharge resistors are different, thus resulting in different time constants for each of said piezoelectric actuators and in different durations of actuation and time to recover their initial state when the energy transfer is interrupted.

18. The system of claim 14, comprising a plurality of secondary resonant coils associated with different electronic components selected so as to build a corresponding plurality of resonant circuits with a corresponding plurality of different resonant frequencies, so as to select different piezoelectric actuators depending on the frequency of the signal supplied to said primary coil.

19. The system of claim 14, said primary coils being supplied with a signal comprising a plurality of different frequencies selected so as to simultaneously drive a corresponding plurality of piezoelectric actuators.

20. The system of claim 14, said primary device comprising a plurality of said primary sets of coils, each set comprising a plurality of primary coils, said electronic supply driver being arranged for supplying different primary sets with different frequencies so as to simultaneously drive a corresponding plurality of piezoelectric actuators.

21. The system of claim 1, said implantable device comprising a moving part with a magnet on said moving part, said system further comprising a sensor for sensing the displacement of said magnet.

22. The system of claim 1, said external device further comprising tertiary coils for detecting displacements of a moving part in said implantable device.

23. The system of claim 1, said implantable device being arranged for implantation within a living body.

24. The secondary device of claim 23, further comprising a valve controlling dispense of a drug within said body, said valve being controlled by said piezoelectric actuator.

25. A medical system comprising:
a medical implant comprising at least one piezoelectric actuator, exclusively passive electronic components including a resonant circuit and arranged for powering and controlling said actuator, and at least one secondary coil; and
an external device having at least one primary coil and an electronic supply driver for supplying primary signals to said primary coil for wireless transfer of energy and control commands between said external device and said medical implant for remote power and control of said piezoelectric actuator;
wherein a direction of displacement of said piezoelectric actuator depends on the phase and/or on the amplitude and/or frequency of at least one first signal supplied to said primary coil,
wherein the direction of displacement of said piezoelectric actuator depends on a direction of a phase shift between one first current supplied to one first coil of said primary set and a second current supplied to one second coil of said primary set.

26. The system of claim 25, wherein said resonant circuit is arranged for moving said piezoelectric actuator in a first direction when at least one said primary signal has a frequency corresponding to the resonance frequency of said resonant circuit, and for moving said piezoelectric actuator in the opposite direction when the frequency of said signal does not correspond to the resonance frequency of said resonant circuit.

27. The system of claim 25, further comprising one discharge resistor in parallel with said piezoelectric actuator.

* * * * *